United States Patent
Champseix

(10) Patent No.: US 9,731,295 B2
(45) Date of Patent: Aug. 15, 2017

(54) FLUID CONNECTION DEVICE FOR BIOLOGICAL ANALYSIS APPARATUSES, SUITABLE FLUIDIC COMPONENT AND BIOLOGICAL ANALYSIS DEVICE EQUIPPED WITH SAME

(71) Applicant: C2 DIAGNOSTICS, Montpellier (FR)

(72) Inventor: Henri Champseix, Montferrier sur Lez (FR)

(73) Assignee: BIT GROUP FRANCE, Montpellier (FR)

( * ) Notice: Subject to any disclaimer, the term of this patent is extended or adjusted under 35 U.S.C. 154(b) by 0 days.

(21) Appl. No.: 14/402,055

(22) PCT Filed: May 17, 2013

(86) PCT No.: PCT/EP2013/060298
§ 371 (c)(1),
(2) Date: Nov. 18, 2014

(87) PCT Pub. No.: WO2013/174762
PCT Pub. Date: Nov. 28, 2013

(65) Prior Publication Data
US 2015/0165437 A1    Jun. 18, 2015

(30) Foreign Application Priority Data
May 22, 2012    (FR) ..................... 12 54633

(51) Int. Cl.
*G01N 33/00* (2006.01)
*B01L 3/00* (2006.01)
(Continued)

(52) U.S. Cl.
CPC ............... *B01L 3/563* (2013.01); *B01L 3/565* (2013.01); *G01N 35/00029* (2013.01);
(Continued)

(58) Field of Classification Search
CPC ......... B01L 3/563; B01L 3/565; G01N 35/29; G01N 35/85; G01N 35/1002
See application file for complete search history.

(56) References Cited

U.S. PATENT DOCUMENTS

| 5,062,310 A | 11/1991 | Eaton |
| 5,279,797 A | 1/1994 | Burns et al. |

(Continued)

FOREIGN PATENT DOCUMENTS

| JP | S61-227848 A | 10/1986 |
| JP | H05-71503 A | 3/1993 |

(Continued)

OTHER PUBLICATIONS

European Office Action from corresponding European Patent Application No. 13728981.5, dated Feb. 20, 2017.
(Continued)

*Primary Examiner* — Sam P Siefke
(74) *Attorney, Agent, or Firm* — Greer, Burns & Crain, Ltd.

(57) ABSTRACT

A fluid connection device is provided for biological analysis apparatuses, intended to simultaneously connect a plurality of fluid conduits and at least one fluidic component including a connecting surface with a plurality of fluid ports, the device having: (i) a holding plate, (ii) removable attachment structure capable of pressing the holding plate against the connecting surface, (iii) connectors suitable for being fixed to the ends of the fluid conduits and provided with a seal suitable for allowing a sealed connection to be made between the connectors and the fluid ports, holding plate including through-openings opposite the fluid ports and being shaped in such a way as to be able to receive the connectors in through-openings and to hold them pressed (Continued)

against the connecting surface. A biological analysis apparatus implementing the device is also provided.

6 Claims, 1 Drawing Sheet

(51) Int. Cl.
    *G01N 35/00*     (2006.01)
    *G01N 35/08*     (2006.01)
    *G01N 35/10*     (2006.01)

(52) U.S. Cl.
    CPC ....... *G01N 35/085* (2013.01); *G01N 35/1002* (2013.01); *G01N 35/1095* (2013.01)

(56) References Cited

U.S. PATENT DOCUMENTS

| | | | |
|---|---|---|---|
| 5,609,195 | A | 3/1997 | Stricklin et al. |
| 5,788,927 | A | 8/1998 | Farrell et al. |
| 6,395,235 | B1 | 5/2002 | Kilcoin et al. |
| 7,311,882 | B1 | 12/2007 | Renzi |
| 7,601,286 | B2 | 10/2009 | Benett et al. |
| 7,963,152 | B2 | 6/2011 | Le Comte et al. |
| 8,677,844 | B2 | 3/2014 | Monsé |
| 2003/0010098 | A1 | 1/2003 | Martin et al. |
| 2009/0023132 | A1 | 1/2009 | Champseix |
| 2009/0142846 | A1 | 6/2009 | Crenshaw et al. |
| 2011/0247405 | A1 | 10/2011 | Yasunaga et al. |
| 2012/0190032 | A1 | 7/2012 | Ness et al. |

FOREIGN PATENT DOCUMENTS

| | | |
|---|---|---|
| JP | 2004-205292 A | 7/2004 |
| RU | 2143686 C1 | 12/1999 |
| RU | 2196989 C1 | 1/2003 |
| RU | 2007101151 A | 7/2008 |
| WO | 2006/121860 A2 | 11/2006 |

OTHER PUBLICATIONS

Japanese Office Action from corresponding Japanese Patent Application No. 2015-513125, dated Mar. 14, 2017.
Russian Office Action from corresponding Russian Patent Application No. 2014151739, dated Mar. 30, 2017.

FLUID CONNECTION DEVICE FOR BIOLOGICAL ANALYSIS APPARATUSES, SUITABLE FLUIDIC COMPONENT AND BIOLOGICAL ANALYSIS DEVICE EQUIPPED WITH SAME

BACKGROUND

The present invention relates to a fluid connection device intended to be used in biological analysis apparatuses. It also relates to suitable fluid components and biological analysis apparatuses equipped with same.

The field of the invention is more particularly but non-limitatively that of systems for the analysis of biological fluids.

Apparatuses for the analysis of biological fluids such as urine, blood, plasma, which make it possible to carry out analyses in an automated manner, are commonly used in laboratories and medical facilities.

In particular blood sample analyzers, or haematology analyzers are known, which make it possible to carry out operations of counting blood cell components such as erythrocytes, leukocytes and platelets.

For example the blood analysis device described in the document WO 2006/103335 is known, which makes it possible to determine in a blood sample, in particular, the total number of leukocytes, the number of leukocytes by sub-population, the number of erythrocytes and platelets, and the haemoglobin level.

Such a device requires the implementation of a set of measurement techniques, such as absorbance measurements, resistivity measurements and optical flow cytometry measurements, on samples prepared beforehand involving dilution and lysis operations etc. As all of the operations must be carried out in an automated manner, it follows that the fluid circuit of such a device is very complex.

Moreover, as these analyses are intended for medical purposes, the operational safety of the device must be optimal in order to limit the risks of incorrect measurements and of contamination, which leads to costly and demanding maintenance commitments.

It is therefore important to optimize the maintainability of the system for managing the fluids (samples, diluents, reagents, etc.). In a standard manner, the components of the fluid circuit (valves, manifolds, containers, etc.) are connected by tubes or flexible pipes, mounted on connectors. The drawback of this type of assembly is that, in order to remove a component from the circuit, it is necessary to disconnect all the pipes, which is tedious and can lead to damage. Another drawback is the presence of pipes on the same side as the fluid components with the risk of disconnection during maintenance of the fluid components.

Document FR 2 891 911 is known, which describes a modular device intended for analyzing biological fluids, in which the fluid components are grouped together in functional modules, with a support in which channels are made. This technique makes it possible to eliminate connections by pipes. However, it has the drawback that all of the channels are grouped together in one and the same module, which imposes major constraints on the design and arrangement of the elements. Moreover, this design poses difficulties for the cleaning and decontamination of the channels, and it is necessary to replace the entire support in the event of a problem.

A subject of the present invention is to propose a fluid connection device for biological analysis apparatuses, which makes it possible to connect fluid components to fluid conduits so that they can easily be disconnected from these conduits.

Another subject of the present invention is to propose a fluid connection device for biological analysis apparatuses, which makes it possible to connect fluid components to fluid conduits which are separate from one another, in order to facilitate the inspection of these conduits and to allow their individual replacement.

Another subject of the present invention is to propose a fluid connection device for biological analysis apparatuses, which makes it possible to arrange the fluid components in an apparatus so that they can be easily accessed by a maintenance operator, without being hindered by the conduits and without the risk of damaging these conduits.

Another subject of the present invention is to propose a fluid connection device which allows the utilization of standardized fluid components, and which can be used in all systems utilizing said fluid connection device.

SUMMARY

This objective is achieved with a fluid connection device for biological analysis apparatuses, intended for simultaneously connecting a plurality of fluid conduits and at least one fluid component comprising a connecting surface with a plurality of fluid ports, characterized in that said device comprises:
  a holding plate,
  removable attachment means capable of pressing said holding plate against said connecting surface,
  connectors suitable for being fixed to the end of the fluid conduits, and provided with sealing means suitable for allowing a sealed connection to be made between said connectors and said fluid ports,
  said holding plate comprising through-openings opposite the fluid ports and being shaped in such a way as to be able to receive said connectors in said through-openings and to hold them pressed against the connecting surface.

According to embodiments, the fluid connection device according to the invention can comprise:
  connectors suitable for being fixed to the end of pipes;
  connectors provided with one or more grooves;
  connectors provided with sealing means comprising an O-ring;
  connectors provided with sealing means comprising a conical surface;
  connectors made of polymer material;
  a holding plate with a substantially flat shape.

According to another aspect, a fluid component for a biological analysis apparatus is proposed, which comprises a connecting surface with a plurality of fluid ports, and which is shaped so as to be suitable for being connected to a plurality of fluid conduits by means of a fluid connection device according to the invention.

The fluid component according to the invention can comprise a connecting surface which groups all the fluid ports together.

According to yet another aspect, a biological analysis apparatus is proposed which comprises a plurality of fluid components according to the invention, fluid conduits comprising flexible pipes and fluid connection interfaces according to the invention.

The biological analysis apparatus according to the invention can comprise a holding plate to which a plurality of fluid components are attached.

It can be intended for carrying out haematology measurements.

BRIEF DESCRIPTION OF THE DRAWINGS

Other advantages and features of the invention will become apparent on reading the detailed description of implementations and embodiments that are in no way limitative, and the following attached drawings.

DETAILED DESCRIPTION

Figure 1:
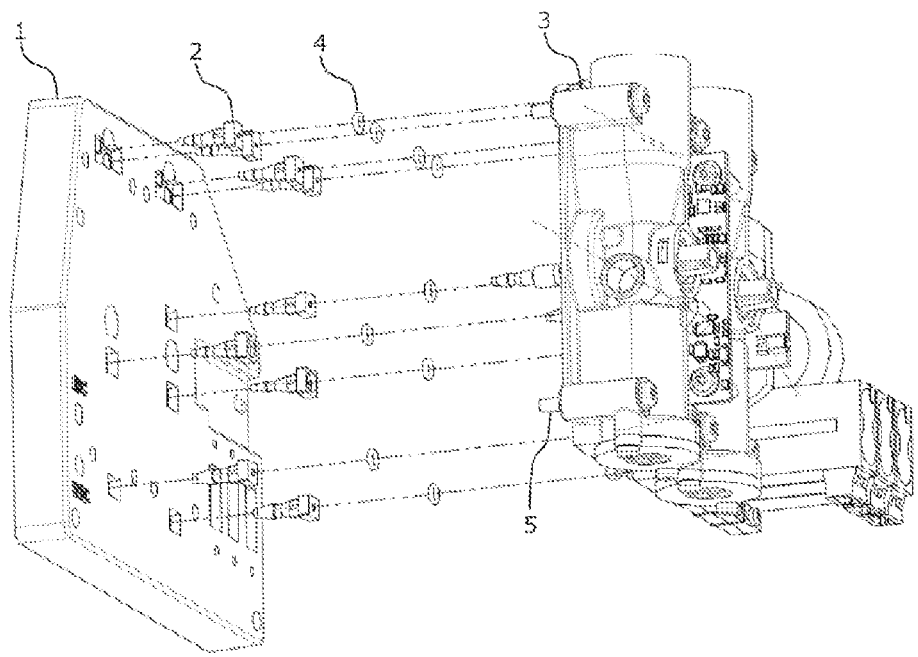
FIG. 1 illustrates an embodiment of a fluid connection device according to the invention.
Figure 2:
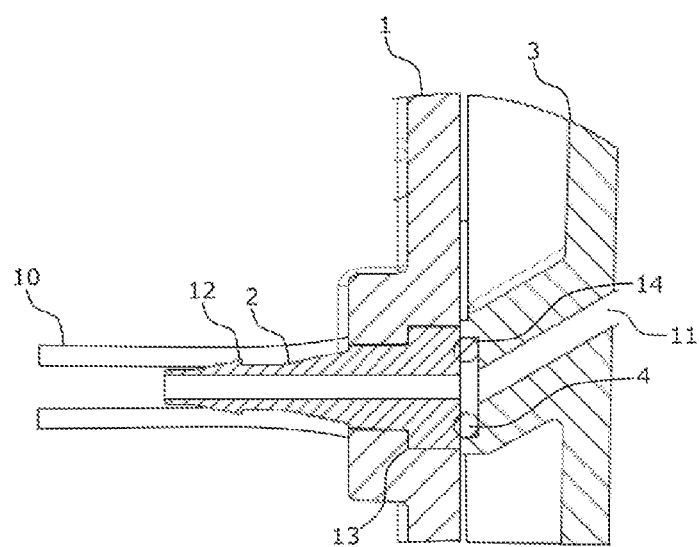
FIG. 2 illustrates a detail of the embodiment of FIG. 1.

With reference to FIGS. 1 and 2, the fluid connection device according to the invention makes it possible to connect a fluid component 3 to fluid conduits 10.

In the embodiment presented, the fluid component 3 is designed so that its fluid ports 11 are grouped together at the level of a connecting surface.

The fluid ports 11 are the channels or conduits through which fluids of interest (biological fluids to be analyzed, diluents, reagents) enter and leave the fluid component 3.

The connection device also comprises a holding plate 1 against which the fluid component 3 can be pressed, on its connecting surface, by means of removable attachment means 5.

These attachment means 5 can be, non-limitatively, screws or clips clamping the fluid component 3 onto the holding plate 1.

The holding plate 1 comprises through-openings into which connectors 2 are inserted. These through-openings are positioned so as to be opposite the fluid ports 11 of the fluid component 3 when the latter is attached to the holding plate 1.

The connectors 2 make it possible to connect fluid conduits 10 to the fluid ports 11 of the fluid component 3 in a sealed manner. These sealed conduits are, in the embodiment presented, flexible pipes made of PVC or any other suitable material.

At one end, the connectors 2 are designed to be inserted into the flexible pipes 10 so as to be firmly held therein. To achieve this they are provided with grooves 12 which hold the pipes 10 and prevent them from being released.

At their other end, the connectors 2 are provided with a shoulder 13 and sealing means which comprise an O-ring 4.

Thus, when the holding plate 1 is pressed against the fluid component 3, it also holds the connectors 2 pressed firmly against the connecting surface of this fluid component 3 so as to make a sealed connection with the corresponding fluid ports 11.

The O-rings are held by a shoulder 14 made in the fluid component 3, thus allowing the dismantling or the replacement of the fluid component 3 without loss of the rings.

The sealing means 4 can also comprise, instead of or in addition to a ring, a conical surface which is inserted and pressed into the fluid port.

The connectors 2 can be produced by moulding or machining, for example from polymer material or from metal.

The holding plate can also be made of any suitable material, for example of polymer material or of metal.

Advantageously, the connectors 2 can be standardized and therefore be mass-produced at low cost. To the extent that they are designed to be difficult to remove from the pipes 10, they can be disposable when the pipes 10 are changed.

The fluid ports 11 can a priori be positioned anywhere on the connecting surface depending on the design constraints of the fluid component 3.

As the mounting plate 1 is simple in shape, it can be easily produced with openings positioned so as to correspond to the position of the fluid ports 11, with simple machining operations and/or by injection of polymer material (plastic).

It is important to note that the fact that the connectors 2 are separate from the mounting plate 1 considerably simplifies, or even completely eliminates, the machining of these components. In fact, producing the mounting plate 1 and the connectors 2 in a single piece would be much more difficult and expensive. In particular this could not be done by moulding because of the grooves 12 if the fluid ports 11 are not arranged in-line.

As explained previously, the fluid connection device according to the invention considerably simplifies handling operations:

In order to remove a fluid component 3, it is sufficient to disconnect it from the holding plate 1, without affecting the fluid conduits or pipes 10 which remain held in position by the holding plate 1;

When a fluid component 3 is remounted, once it is clamped against the holding plate 1, the fluid connections between the pipes 11 and the fluid ports 11 are automatically re-established;

The fluid conduits 10 can also be manipulated very easily. In fact, when the fluid component 3 is removed, a pipe 10 optionally with a connector 2 mounted at the end can easily be removed or replaced by passing it through the opening in the holding plate 1.

The fluid connection device according to the invention thus makes it possible to retain the advantages of a fluid system design in which the fluid components 3 are connected by flexible pipes 10 (such as for example ease of integration and modularity), whilst avoiding the problems of cutting the pipes 10 during maintenance.

It is possible to design an apparatus by arranging the essential fluid components 3 so that they can be easily accessed by an operator for exchange or maintenance without his being hindered by the fluid conduits 10. The fluid components 3 can for example be placed on one face of a holding plate 1 that is directly accessible when the apparatus is opened, with all the conduits 10 arranged on the other side of this holding plate 1.

The fluid connection device according to the invention can of course be used in any analysis system utilizing fluid components 3.

By way of a non-limitative example, it may in particular be utilized in order to produce a blood analyzing device, as described in the document WO 2006/103335, which makes it possible to determine the total number of leukocytes in a blood sample, a distribution of these leukocytes into sub-populations, number of erythrocytes and platelets, and haemoglobin level.

In this case, the fluid components 3 can comprise in particular:

reservoirs intended for receiving the blood sample, and/or for carrying out dilution and lysis operations, a set of measurement tanks for carrying out electrical impedance and/or optical flow cytometry measurement operations, in order to count cells, syringes for moving the fluids, valves and manifolds for configuring the hydraulic circuit depending on the operations.

Of course, the invention is not limited to the examples which have just been described, and numerous adjustments can be made to these examples without exceeding the scope of the invention.

The invention claimed is:

1. A fluid connection device for biological analysis apparatuses configured for simultaneously connecting a plurality of fluid conduits and at least one fluid component having a connecting surface with a plurality of fluid ports, said device comprising:
   a holding plate having an outer surface;
   at least one removable attachment device configured to press and secure said holding plate against said connecting surface;
   connectors fixed to the ends of the fluid conduits, wherein end surfaces of said connectors are substantially flush with said outer surface of said holding plate; and
   a seal positioned between each of said connectors and a corresponding one of the fluid ports, said seal being configured for forming a sealed connection between said connectors and said fluid ports; and
   said holding plate comprising through-openings opposite the fluid ports and being shaped to receive said connectors in said through-openings and to hold said connectors pressed against the connecting surface.

2. The fluid connection device of claim 1, wherein said connectors include one or more grooves.

3. The fluid connection device of claim 1, wherein said seal comprises an O-ring.

4. The fluid connection device of claim 1, wherein said seal comprises a conical surface.

5. The fluid connection device of claim 1, wherein said connectors are made of polymer material.

6. The fluid connection device of claim 1, which said holding plate has a substantially flat shape.

* * * * *